United States Patent
Crank

(10) Patent No.: US 9,814,837 B2
(45) Date of Patent: Nov. 14, 2017

(54) INJECTION TUBE FOR JET INJECTION DEVICE

(71) Applicant: AMS Research Corporation, Minnetonka, MN (US)

(72) Inventor: Justin M. Crank, Maple Grove, MN (US)

(73) Assignee: ASTORA WOMEN'S HEALTH HOLDINGS, LLC, Minnetonka, MN (US)

( * ) Notice: Subject to any disclaimer, the term of this patent is extended or adjusted under 35 U.S.C. 154(b) by 0 days.

(21) Appl. No.: 14/515,757

(22) Filed: Oct. 16, 2014

(65) Prior Publication Data

US 2015/0038789 A1 Feb. 5, 2015

Related U.S. Application Data

(63) Continuation of application No. 11/944,081, filed on Nov. 21, 2007, now abandoned.

(Continued)

(51) Int. Cl.
*A61M 5/30* (2006.01)
*A61M 25/00* (2006.01)
(Continued)

(52) U.S. Cl.
CPC .......... *A61M 5/3007* (2013.01); *A61B 1/307* (2013.01); *A61M 25/005* (2013.01);
(Continued)

(58) Field of Classification Search
CPC . A61B 1/307; A61M 25/005; A61M 25/0075; A61M 39/08; A61M 5/30; A61M 5/3007
See application file for complete search history.

(56) References Cited

U.S. PATENT DOCUMENTS

| 2,687,131 A | 9/1952 | Raiche |
| 3,425,413 A | 2/1969 | Stephens |

(Continued)

FOREIGN PATENT DOCUMENTS

| WO | WO 96/16606 | 6/1996 |
| WO | WO 97/31667 | 9/1997 |

(Continued)

OTHER PUBLICATIONS

Watson, Patel & DiTrolio, "Transurethral Ethanol Ablation of the Prostate," The Journal of Urology, vol. 161, No. 4, Supplement, p. 305, Apr. 1999.

(Continued)

*Primary Examiner* — Imani Hayman
(74) *Attorney, Agent, or Firm* — Kagan Binder, PLLC

(57) ABSTRACT

A non-metal, polymeric tubular device for delivering a therapeutic fluid to a treatment site within a patient. The non-metal, polymeric tubular device can be fabricated using suitable high strength polymers and in some versions can be reinforced through the inclusion of reinforcement materials or braiding. The non-metal, polymeric tubular device can be fabricated so as to have a burst strength exceeding at least about 2,000 psi. The non-metal, polymeric tubular device can be fabricated so as to have distention properties, wherein an orifice or jet port located at a distal end of the polymeric tubular device retains its shape and/or size without suffering swelling that can have a detrimental impact on a fluid jet used to deliver the therapeutic fluid at the treatment site.

17 Claims, 2 Drawing Sheets

Related U.S. Application Data

(60) Provisional application No. 60/866,741, filed on Nov. 21, 2006.

(51) Int. Cl.
*A61M 39/08* (2006.01)
*A61B 1/307* (2006.01)

(52) U.S. Cl.
CPC ........ *A61M 25/0075* (2013.01); *A61M 39/08* (2013.01); *A61M 5/30* (2013.01)

(56) References Cited

U.S. PATENT DOCUMENTS

| | | | |
|---|---|---|---|
| 3,905,361 A | 9/1975 | Hewson et al. |
| 4,116,201 A | 9/1978 | Shah |
| 4,430,076 A | 2/1984 | Harris |
| 4,763,654 A | 8/1988 | Jang |
| 4,811,847 A | 3/1989 | Reif et al. |
| 4,827,907 A | 5/1989 | Tashiro |
| 4,867,742 A | 9/1989 | Calderon |
| 4,958,634 A | 9/1990 | Jang |
| 5,007,897 A | 4/1991 | Kalb et al. |
| 5,033,998 A | 7/1991 | Corday et al. |
| 5,158,540 A | 10/1992 | Wijay et al. |
| 5,221,258 A | 6/1993 | Shturman |
| 5,257,977 A | 11/1993 | Eshel |
| 5,322,503 A | 6/1994 | Desai |
| 5,336,178 A | 8/1994 | Kaplan et al. |
| 5,423,745 A | 6/1995 | Todd et al. |
| 5,441,485 A | 8/1995 | Peters |
| 5,458,571 A | 10/1995 | Lampropoulos et al. |
| 5,501,666 A | 3/1996 | Spielberg |
| 5,562,703 A | 10/1996 | Desai |
| 5,569,219 A | 10/1996 | Hakki et al. |
| 5,588,960 A | 12/1996 | Edwards et al. |
| 5,637,086 A | 6/1997 | Ferguson et al. |
| 5,823,940 A | 10/1998 | Newman |
| 5,840,061 A | 11/1998 | Menne et al. |
| 5,861,002 A | 1/1999 | Desai |
| 5,876,373 A | 3/1999 | Giba et al. |
| 5,904,147 A | 5/1999 | Conlan et al. |
| 5,919,163 A | 7/1999 | Glickman |
| 5,964,756 A | 10/1999 | McGaffigan et al. |
| 6,132,395 A | 10/2000 | Landau et al. |
| 6,231,591 B1 | 5/2001 | Desai |
| 6,280,413 B1 | 8/2001 | Clark et al. |
| 6,280,414 B1 | 8/2001 | Shah et al. |
| 6,344,027 B1 | 2/2002 | Goll |
| 6,400,980 B1 | 6/2002 | Lemelson |
| 6,461,296 B1 | 10/2002 | Desai |
| 6,514,247 B1 | 2/2003 | McGaffigan et al. |
| 6,547,767 B1 | 4/2003 | Moein |
| 6,602,241 B2 | 8/2003 | Makower et al. |
| 6,607,510 B2 | 8/2003 | Landau |
| 6,610,007 B2 | 8/2003 | Belson et al. |
| 6,641,553 B1 | 11/2003 | Chee et al. |
| 6,645,170 B2 | 11/2003 | Landau |
| 6,689,103 B1 | 2/2004 | Palasis |
| 6,709,427 B1 | 3/2004 | Nash et al. |
| 6,716,190 B1 | 4/2004 | Glines et al. |
| 6,752,799 B2 | 6/2004 | Grund et al. |
| 6,905,475 B2 | 6/2005 | Hauschild et al. |
| 6,939,381 B2 | 9/2005 | Stark et al. |
| 6,960,182 B2 | 11/2005 | Moutafis |
| 6,964,649 B2 | 11/2005 | Goll |
| 6,974,441 B2 | 12/2005 | Ravo |
| 6,989,103 B2 | 1/2006 | Mohsen et al. |
| 7,015,253 B2 | 3/2006 | Escandon et al. |
| 7,060,051 B2 | 6/2006 | Palasis |
| 7,182,745 B2 | 2/2007 | Desmond, III |
| 7,214,220 B2 | 5/2007 | McGlinch et al. |
| 7,419,482 B2 | 9/2008 | Nash et al. |
| 7,594,900 B1 * | 9/2009 | Nash et al. .............. 604/27 |
| 7,981,074 B2 | 7/2011 | Davis et al. |
| 2003/0191449 A1 | 10/2003 | Nash et al. |
| 2004/0111055 A1 | 6/2004 | Daellenbach |
| 2004/0193097 A1 | 9/2004 | Hofmann et al. |
| 2005/0234388 A1 | 10/2005 | Amos et al. |
| 2006/0074383 A1 | 4/2006 | Boulais |
| 2006/0129125 A1 | 6/2006 | Copa et al. |
| 2006/0200226 A1 | 9/2006 | Furst et al. |
| 2006/0241564 A1 | 10/2006 | Corcoran et al. |
| 2006/0264898 A1 | 11/2006 | Beasley et al. |
| 2007/0078435 A1 | 4/2007 | Stone et al. |
| 2007/0106208 A1 | 5/2007 | Uber et al. |
| 2008/0119823 A1 | 5/2008 | Crank |
| 2012/0277721 A1* | 11/2012 | Hauschild ........ A61B 17/32037 604/500 |

FOREIGN PATENT DOCUMENTS

| | | |
|---|---|---|
| WO | WO 00/66199 | 11/2000 |
| WO | WO 00/67647 | 11/2000 |
| WO | WO 01/10313 | 2/2001 |
| WO | WO 01/36029 | 5/2001 |
| WO | WO 01/41656 | 6/2001 |
| WO | WO 01/41657 | 6/2001 |
| WO | WO 03/030756 | 4/2003 |
| WO | WO 2007/038591 | 4/2007 |

OTHER PUBLICATIONS

DiTrolio, J.V., "Chemoablation of the Prostate with Dehydrated Ethanol for the Treatment of BPH," presented at the 5th International Consultation on BPH, Paris, France, Jun. 2000.

* cited by examiner

INJECTION TUBE FOR JET INJECTION DEVICE

PRIORITY CLAIM

The present application is a continuation U.S. Ser. No. 11/944,081, filed Nov. 21, 2007, which in turn claims priority to U.S. Provisional Patent Application No. 60/866,741, filed Nov. 21, 2006 and entitled, "INJECTION TUBE FOR JET INJECTION DEVICE," which applications are herein incorporated by reference in their entireties.

FIELD OF THE INVENTION

The present invention relates generally to jet injection devices for the delivery of therapeutic fluids to a treatment site. More specifically, the present invention relates to a non-metal reinforced polymeric injection tube having performance characteristics compatible with minimally invasive jet injection devices.

BACKGROUND OF THE INVENTION

A wide variety of medical treatments are at least partially performed through the delivery and introduction of therapeutic compositions to a treatment location. In home or outpatient settings, typical delivery methods can comprise oral delivery, via liquid or solid forms, as well as a variety of inhalant style devices. In clinical or hospital settings, therapeutic fluids can be injected using needle based or in some minimally invasive procedures, the therapeutic fluid can be delivered through a tubular device such as a catheter or endoscope based systems.

One way in which therapeutic fluids can be delivered internally is through the use of a tubular device configured to provide a jet-injection of the therapeutic fluid at a desired treatment site. Generally, a remote injector is utilized to deliver the therapeutic fluid from an external reservoir located at a proximal end of the tubular device such administration can occur at a distal end of the tubular device. Due to the relatively long travel length of the therapeutic fluid through the tubular device, the remote injector must generally be capable of pressurizing the therapeutic fluid to pressures exceeding about 2,000 psi. In order to accommodate these pressures, the tubular devices have been fabricated of alloys such as NiTi or stainless steel or with metal-reinforced polymers such as the braided tubes typically found in catheters. While the use of alloys and metal reinforced polymers satisfy the operational requirements related to burst pressure and distention strength, they are generally of limited flexibility making them difficult to navigate within the tortuous paths often found in the human body such as, for example, the urogenital tract.

SUMMARY OF THE INVENTION

The present invention comprises a non-metal, polymeric tubular device for delivering a therapeutic fluid to a treatment site within a patient. The non-metal, polymeric tubular device can be fabricated using suitable high strength polymers including, for example, polyimide, polyetherimide available from General Electric under the trade name Ultem® and linear aromatic polymers such as PEEK™ available from Victrex plc. In some embodiments, the non-metal, polymeric tubular device can be reinforced through the inclusion of materials including nano-particles, clays and/or glass. In some presently contemplated embodiments, the non-metal, polymeric tubular device can be reinforced with one or more polymers such as, for example, tubes braided with carbon fiber, synthetic para-aramid fiber such as Kevlar available from E.I. du Pont de Nemours and Company or other high-strength polymers. The non-metal, polymeric tubular device can be fabricated so as to have a burst strength exceeding at least about 2,000 psi and in some embodiments, having a burst strength within a range of about 2,000 psi to about 5,000 psi. The non-metal, polymeric tubular device can be fabricated so as to have distention properties, wherein an orifice or jet port located at a distal end of the polymeric tubular device retains its shape and/or size without suffering swelling that can have a detrimental impact on a fluid jet used to deliver the therapeutic fluid at the treatment site.

In one aspect, the present disclosure is directed to a non-metal, polymeric tubular device for delivering a therapeutic fluid to a treatment site within the body wherein the non-metal, polymeric tubular device has a burst strength within a range of about 2,000 psi to about 5,000 psi. The non-metal, polymeric tubular device can be fabricated using suitable high strength polymers including, for example, polyimide, polyetherimide available from General Electric under the trade name Ultem® and linear aromatic polymers such as PEEK™ available from Victrex plc. In some embodiments, the non-metal, polymeric tubular device can be reinforced through the inclusion of materials including nano-particles, clays and/or glass. In some presently contemplated embodiments, the non-metal, polymeric tubular device can be reinforced with one or more polymers such as, for example, tubes braided with carbon fiber, synthetic para-aramid fiber such as Kevlar available from E.I. du Pont de Nemours and Company or other high-strength polymers. In some embodiments, the non-metal, polymeric tubular device can have a tube length ranging from about 18 to about 72 inches. In some embodiments, the non-metal, polymeric tubular device can include an orifice functioning as a jet nozzle, wherein the non-metal, polymeric tubular device has sufficient strength to avoid distention at the orifice.

In another aspect, the present disclosure is directed to a method of delivering a therapeutic fluid comprising providing a non-metal, polymeric tubular device having a burst strength range of about 2,000 psi to about 5,000 psi, delivering the therapeutic fluid through the non-metal, polymeric tubular device and administering the therapeutic fluid to the treatment site with a jet orifice located at a distal end of the non-metal, polymeric tubular device. The method can further comprise positioning the non-metal, polymeric tubular device through an internal lumen within a patient such as a patient's urogenital tract.

In yet another aspect of the present disclosure, a therapeutic fluid delivery system can comprise an injector device and a non-metal, polymeric tubular device for delivery a therapeutic fluid to a treatment location within a patient's body. The non-metal, polymeric tubular device can have a burst strength ranging from about 2,000 psi to about 5,000 psi so as to prevent tube failure and to similarly, avoid distention at a jet orifice located at a distal end of the non-metal, polymeric tubular device.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
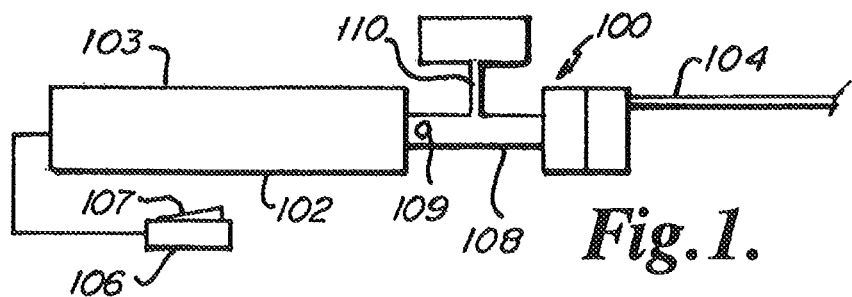
FIG. 1 is a perspective view of an embodiment of a therapeutic fluid delivery system for delivering a therapeutic fluid to a treatment location according to the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF THE DRAWINGS

In the following detailed description of the present invention, numerous specific details are set forth in order to provide a thorough understanding of the present invention. However, it will be obvious to one skilled in the art that the present invention may be practiced without these specific details. In other instances, well-known methods, procedures, and components have not been described in detail so as to not unnecessarily obscure aspects of the present invention.

A needleless fluid delivery system 100 is illustrated generally in FIG. 1. Needleless fluid delivery system 100 can comprise an injector 102 and an applicator lumen 104. Injector 102 can be as simple as manually activated syringe or injector 102 can comprise an automated injector 103 including a user interface 106 and a connector member 108. Connector member can include a surface opening 109 and a therapeutic fluid supply 110. User interface 106 can comprise an input means for selectively delivering a pressurized fluid through the connector member 108. Representative input means can include foot pedal 107, switches, buttons or a touch-screen capable of receiving touch commands as well as displaying system information including a mode of operation as well as operating parameters.

Figure 2:
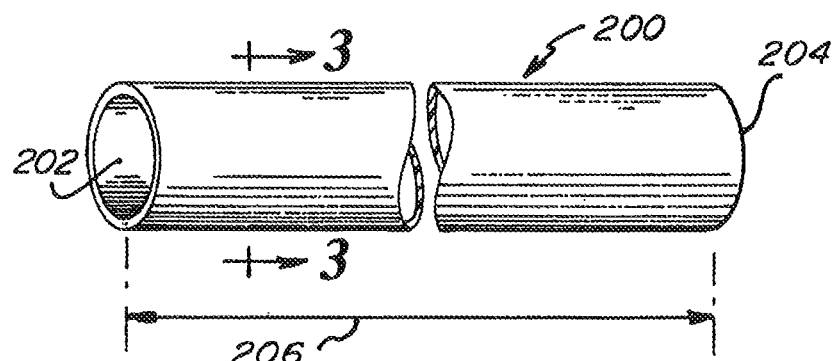
FIG. 2 is a side view of an embodiment of a non-metal, polymeric tubular device according to the present disclosure.
Figure 3A:
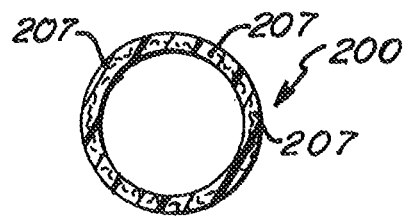
FIG. 3a is a section view of the non-metal, polymeric tubular device of FIG. 2 taken at line 3-3 of FIG. 2.

As seen in FIGS. 2 and 3a, the applicator lumen 104 can comprise a non-metal, polymeric tubular device 200 having a proximal attachment end 202 and a distal treatment end 204. Non-metal, polymeric tubular device 200 can have a tube length 206 that corresponds to a type of treatment to be performed within a patient's body. For example, when non-metal, polymeric tubular device 200 is configured to perform a cytoscopic or endoscopic procedure, the tube length 206 can range from about 18 to about 72 inches in length.

Figure 3B:
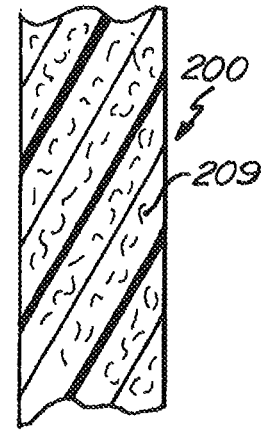
FIG. 3b is a side view of a portion of an embodiment of a non-metal, polymeric tubular device according to the present disclosure.

Non-metal, polymeric tubular device 200 is generally formed so as to have a burst strength of at least about 2,000 psi. In a preferred embodiment, the non-metal, polymeric tubular device is formed to have a burst strength ranging from about 2,000 psi to about 5,000 psi. In one representative embodiment, non-metal, polymeric tubular device 200 is formed of a single high strength polymer such as, for example, a polyimide, polyetherimide available from General Electric under the trade name Ultem® and linear aromatic polymers such as PEEK™ available from Victrex plc. Alternatively, the non-metal, polymeric tubular device 200 can be formed from a reinforced polymer that is reinforced with reinforcing materials 207 such as, for example, nano-particles, clays or glass. In another embodiment as shown in FIG. 3b, the non-metal, polymeric tubular device 200 is reinforced with a reinforcing fiber 209 such as, for example, tubes braided with carbon fiber, synthetic para-aramid fiber such as Kevlar available from E.I. du Pont de Nemours and Company or other high-strength polymers braided within non-metal, polymeric tubular device 200. Generally, the non-metal, polymeric tubular device 200 is extruded though other appropriate fabrication methods including molding can be utilized as well.

Figure 4:
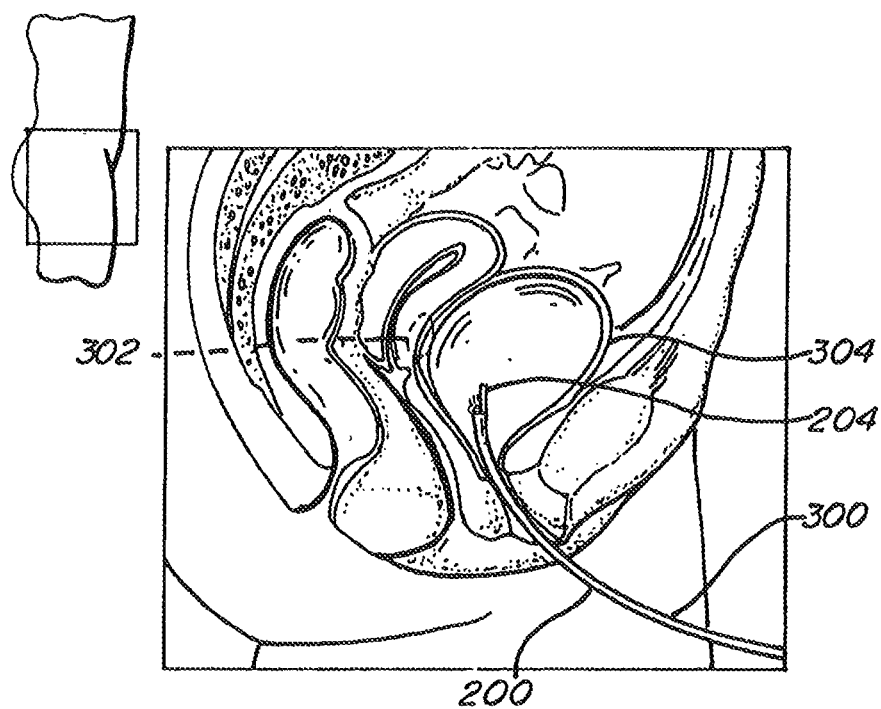
FIG. 4 is an illustration of the non-metal, polymeric tubular device positioned for delivery of a therapeutic fluid within a patient's urogenital tract.

As illustrated in FIG. 4, non-metal, polymeric tubular device 200 can be configured as a cytoscope 300 to deliver therapeutic fluid to a treatment location 302 such as, for example, the urinary bladder 304. Distal treatment end 204 generally accesses the urogenital tract through the urethra 306 wherein the distal treatment end 204 enters the urinary bladder 304. Cytoscope 300 can include a fiber optic scope such that a medical professional can verify the distal treatment end 204 is positioned proximate the treatment location 302.

In positioning the non-metal polymeric tubular device 200 at treatment location 302, it will be understood that a medical professional frequently employs a medical imaging system such as, for example, computer axial tomography (CAT), magnetic resonance imaging (MRI), or in the case of treatment of a prostate gland, the preferred imaging means is transrectal ultrasound (TRUS) so as to achieve the desired position of administration orifice 208. Through the use of a medical imaging system, a medical professional can verify that the therapeutic fluid is in fact administered at the treatment location 302.

Figure 6:
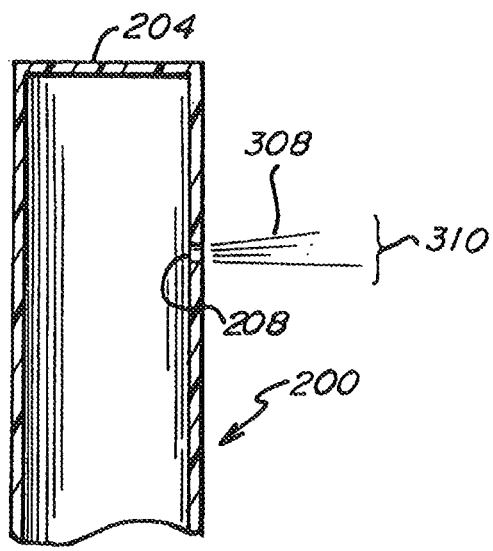
FIG. 6 is a side view of a non-metal, polymeric tubular device of the present invention delivering a therapeutic fluid through jet injection from a jet orifice at a distal end of the non-metal, polymeric tubular device.

Once the distal treatment end 204, and more specifically, the administration orifice 208 is positioned with respect to the treatment location 302, the injector 102 can be actuated so as to begin delivery of a therapeutic fluid 308 as illustrated in FIG. 6. Generally, injector 102 directs therapeutic fluid 308 through the non-metal, polymeric tubular device 200 at low velocities and high pressures generally between about 2,000 psi to about 5,000 psi. The high pressures supplied by the injector 102 are necessary due to the pressure losses experienced in the relatively, small diameter non-metal, polymeric tubular device 200. As the therapeutic fluid 308 reaches distal treatment end 204, the therapeutic fluid 308 is rapidly accelerated through the administration orifice 208 to form a fluid jet 310. Using fluid jet 310, therapeutic fluid 308 can be controllably dispensed directly at the treatment location 302 so as to reduce the potential for exposure to other non-desired areas. As the fluid jet 310 moves away from the administration orifice 208, the pressure of fluid jet 310 is rapidly lost.

Figure 5:
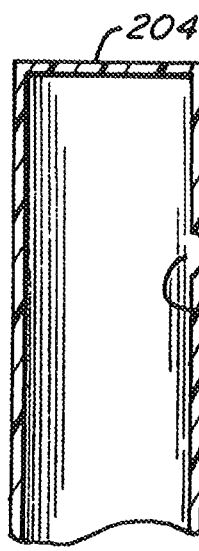
FIG. 5 is a side view of a prior art polymeric tube suffering distention at a jet orifice located at a distal end of the prior art polymeric tube.

By using non-metal, polymeric tubular device 200, problems associated with using conventional polymeric tubing can be avoided. With reference to FIG. 5, conventional polymeric tubing 400 can suffer a variety of failure modes including, for example, distention or swelling of the conventional polymeric tubing 400 at an administration orifice 402. When distention occurs, the changing dimensional characteristics of the administration orifice cause uncontrolled variations in the characteristics of a fluid jet 404 as well as potential failure and rupture of the conventional polymeric tubing 400.

While the invention is amenable to various modifications and alternative forms, specifics thereof have been shown by way of example in the drawings and will, be described in detail. It should be understood, however, that the intention is not to limit the invention to the particular embodiments described. On the contrary, the intention is to cover all modifications, equivalents, and alternatives.

The invention claimed is:

1. A needleless non-metal, polymeric tubular injection device for delivering a therapeutic fluid to a treatment location within a patient's body, the device comprising an applicator body defining a lumen and a sidewall, the applicator body including a distal end and a proximal connection end, wherein an administration orifice is positioned through the sidewall proximate the distal end; wherein the applicator body comprises a polymer selected from a group consisting of: a polyimide polymer, a polyetherimide polymer, and a polyether ether ketone; wherein the applicator body exhibits a burst strength of at least 2,000 pounds per square inch; in combination with a cystoscope; wherein the applicator body extends distally from a distal end of the cystoscope such that the administration orifice may be positioned with unobstructed access to tissue of a urogenital tract to inject therapeutic fluid into the tissue of the urogenital tract for the injected therapeutic fluid to remain in the tissue in the patient's body.

2. The non-metal, polymeric tubular device of claim 1 wherein the applicator body is fabricated of a single polymer selected from the group consisting of polyimide polymer, polyetherimide polymer, and polyether ether ketone.

3. The non-metal, polymeric tubular device of claim 1 wherein the applicator body comprises an extruded applicator body having a length of about 18 inches to about 72 inches and a substantially uniform diameter along the tube length.

4. The non-metal, polymeric tubular device of claim 1 wherein the applicator body is formed of a non-reinforced polyether ether ketone polymer.

5. The non-metal, polymeric tubular device of claim 1 wherein the applicator body is formed of reinforced polyether ether ketone polymer.

6. The non-metal, polymeric tubular device according to claim 1 wherein the distal end, the applicator body, and the administration orifice are configured to eject fluid from the administration orifice laterally to transurethrally penetrate and treat a prostate gland.

7. The non-metal, polymeric tubular device according to claim 1 comprising a fiber optic scope adapted to view the injection orifice relative to a treatment location.

8. A needleless injection system comprising the non-metal, polymeric tubular device of claim 1 and further comprising
an injector.

9. The needleless fluid delivery system of claim 8 wherein the injector comprises an automated injector having a user interface and a connector member attachable to the proximal connection end.

10. The needleless fluid delivery system according to claim 9 wherein the proximal connection end engages the automated injector independently of the cystoscope, and a length of the applicator lumen extends between the automated injector and the cystoscope.

11. The needleless fluid delivery system according to claim 10 wherein the applicator body is extruded polymer and has a length of about 18 inches to about 72 inches and a substantially uniform diameter along the length.

12. The needleless fluid delivery system of claim 8 wherein the applicator body is fabricated of a single polymer selected from the group consisting of polyimide polymer, polyetherimide polymer, and polyether ether ketone.

13. The needleless fluid delivery system of claim 8 wherein the distal end, applicator body, and administration orifice are configured to eject fluid from the administration orifice laterally to transurethrally penetrate and treat a prostate gland.

14. The needleless fluid delivery system according to claim 8 wherein the tissue is bladder tissue.

15. The needleless fluid delivery system according to claim 8 comprising a fiber optic scope adapted to view the injection orifice relative to a treatment location.

16. A method of injecting a therapeutic fluid into tissue of a urogenital tract of a patient, the method comprising
providing a device according to claim 1,
passing the distal end within a urethra of the patient,
positioning the distal end at a treatment location such that the administration orifice is positioned to inject therapeutic fluid into the tissue, and
injecting therapeutic fluid into the tissue, with the therapeutic fluid remaining in the tissue in the patient's body.

17. The method according to claim 16 wherein the tissue is bladder tissue.

* * * * *